(12) United States Patent
Teramura

(10) Patent No.: US 7,551,817 B2
(45) Date of Patent: Jun. 23, 2009

(54) PROBE AND OPTICAL TOMOGRAPHY SYSTEM

(75) Inventor: Yuichi Teramura, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 11/730,883

(22) Filed: Apr. 4, 2007

(65) Prior Publication Data

US 2007/0232902 A1 Oct. 4, 2007

(30) Foreign Application Priority Data

Apr. 4, 2006 (JP) ............... 2006-103440

(51) Int. Cl.
*G02B 6/26* (2006.01)
*G02B 6/34* (2006.01)
*G01B 11/02* (2006.01)
(52) U.S. Cl. .................... 385/31; 385/36; 356/477
(58) Field of Classification Search ............ None
See application file for complete search history.

(56) References Cited

U.S. PATENT DOCUMENTS 5,409,483 A * 4/1995 Campbell et al. ............ 606/15

6,134,003 A * 10/2000 Tearney et al. ............ 356/479

FOREIGN PATENT DOCUMENTS

| JP | 4-135550 A | 5/1992 |
| JP | 6-165784 A | 6/1994 |
| JP | 2003-139688 A | 5/2003 |

OTHER PUBLICATIONS

Motion artifacts in optical coherence tomography with frequency-domain ranging, S.H. Yun et al., *Optics Express*, vol. 12, No. 13, pp. 2977-2998, Jun. 28, 2004.
"Optical Frequency Scanning Interference Microscopes", M. Takeda, *Optics Engineering Contact*, vol. 41, No. 7, pp. 426-432, 2003 and its partial translation.

* cited by examiner

*Primary Examiner*—Omar Rojas
(74) *Attorney, Agent, or Firm*—Sughrue Mion, PLLC

(57) ABSTRACT

An optical fiber is disposed in the direction of axis of the outer envelope inside a tubular outer envelope. Light emitted from the front end of the optical fiber is collected and projected on a body-to-be-scanned disposed externally of the outer envelope, and converged on the body-to-be-scanned. The outer envelope is filled with liquid so that the optical fiber is in the liquid.

3 Claims, 8 Drawing Sheets

PROBE AND OPTICAL TOMOGRAPHY SYSTEM

BACKGROUND OF THE INVENTION

1. Field of the Invention

This invention relates to an optical probe, and more particularly to an optical probe having a tubular outer envelope and having a function of emitting light from the peripheral surface thereof and an optical tomography system where such an optical probe is employed.

2. Description of the Related Art

As a conventional method for obtaining tomographic images of measurement targets, such as living tissue, a method that obtains optical tomographic images by OCT (Optical Coherence Tomography) measurement has been proposed (refer to Japanese Unexamined Patent Publication Nos. 6(1994)-165784 and 2003-139688). The OCT measurement is a type of light interference measurement method that utilizes the fact that light interference is detected only when the optical path lengths of divided light beams, that is, a measurement light beam and a reference light beam, match within a range of coherence length of a light source. That is, in this method, a low coherent light beam emitted from a light source is divided into a measuring light beam and a reference light beam, the measuring light beam is irradiated onto a measurement target, and the measurement light beam reflected by the measurement target is led to a combining means. Whereas the reference light beam is led to the combining means after its optical path length is adjusted so that its optical path length equalizes to that of the reflected light from an arbitrary position in the object. Then the measuring light and the reference light are combined by the combining means, and the intensities thereof are detected by the light detector.

In order to obtain a one-dimensional tomographic image, an interference strength waveform according to the reflectance distribution along the same axis as the direction of travel of the measuring light by scanning the optical path length of the measuring light according to the measuring area. That is, a reflected light intensity distribution according to the structure in the direction of depth of the object to be measured can be obtained. Further, when the projecting position of the measuring light applied to the object is one-dimensionally scanned in a direction perpendicular to the optical axis by the use of a deflecting means or a physical means, a two dimensional tomography representing a reflected light intensity distribution can be obtained. Further, when the projecting position of the measuring light is two-dimensionally scanned in directions perpendicular to the optical axis, a three dimensional tomography representing a reflected light intensity distribution can be obtained.

In the above OCT system, a tomographic image is obtained by changing the optical path length of the reference light, thereby changing the measuring position (the depth of measurement) in the object. This technique is generally referred to as "TD-OCT (time domain OCT)". More specifically, in the optical path length adjusting mechanism for the reference light disclosed in Japanese Unexamined Patent Publication No. 6(1994)-165784, an optical system which collects the reference light emitted from the optical fiber on a mirror is provided and the optical path length is adjusted by moving only the mirror in the direction of the optical axis of the reference light. Further, in the optical path length changing mechanism for the reference light disclosed in Japanese Unexamined Patent Publication No. 2003-139688, the reference light emitted from the optical fiber is turned to parallel light by a lens, the reference light in the form of parallel light is collected and caused to enter the optical fiber again by an optical path length adjusting lens, and the optical path length adjusting lens is moved back and forth in the direction of the beam axis of the reference light.

Whereas, as a system for rapidly obtaining a tomographic image without changing the optical path length of the reference light, there has been proposed an optical tomography system for obtaining an optical tomographic image by measurement of SD-OCT (spectral domain OCT). In the SD-OCT system, a tomographic image which is one-dimensional in the optical axis is formed without physically scanning the optical path length, by dividing broad band, low coherent light into measuring light and reference light by the use of an interferometer as in the above-described TD-OCT system, substantially equalizing the measuring light and the reference light to cause them to interfere with each other, decomposing the interference light into the optical frequency components, measuring the intensity of the interference light by the optical frequency components by an array type detector and carrying out a Fourier analysis on the obtained spectral interference waveforms by a computer. As in above-described TD-OCT system, a two-dimensional or a three-dimensional tomographic image can be obtained by scanning the projecting position of the measuring light in directions perpendicular to the optical axis.

As another system for rapidly obtaining a tomographic image without changing the optical path length of the reference light, there has been proposed an optical tomography system for obtaining an optical tomographic image by measurement of SS-OCT (swept source OCT) (refer to "Motion artifacts in optical coherence tomography with frequency-domain ranging", S. H. Yun et al., *OPTICS EXPRESS*, Vol. 12, No. 13, pp. 2977-2998, 2004.). The SS-OCT system employs a light frequency tunable laser as a light source. The high coherence laser beam is divided into measuring light and reference light. The measuring light is projected onto the object and the reflected light from the object is led to the combining means. The reference light is led to the combining means after it is made substantially equal to the measuring light in the optical path length to cause the measuring light and the reference light to interfere with each other, and the measuring light and the reference light are combined by the combining means. The intensity of the combined light is detected by an optical detector. The intensity of the interference light is measured by the frequency component by sweeping the frequency of the light frequency tunable laser and a one-dimensional tomography in the optical axis is formed without physically scanning the optical path length by Fourier-transforming the spectral interference waveform thus obtained with a computer. As in above-described TD-OCT system, a two-dimensional or a three-dimensional tomographic image can be obtained by scanning the projecting position of the measuring light in directions perpendicular to the optical axis.

There has been investigated application of the optical tomography system of each of the systems described above to a measurement in an organic body by a combination of an endoscope. In the optical tomography system of each of the systems described above, a tomographic image along a certain surface of the object is generally obtained and it is necessary to at least one-dimensionally scan the measuring light beam in the object in perpendicular to the optical axis for this purpose. As a means for effecting such a light scanning, there has been known, as disclosed in Japanese Unexamined Patent Publication No. 4(1992)-135550, an optical probe having a tubular outer envelope and having a function of deflecting light emitted from the peripheral surface thereof in the direction of circumference of the outer envelope. More specifically, the optical probe comprises an inserting portion (outer envelope) which is inserted into the sample, a rotatable hollow shaft which is inserted inside the outer envelope, an optical fiber which is passed through the shaft, and a light deflecting element which is connected to the front end portion of the shaft to be rotated together therewith and deflects light radiated from the front end portion of the optical fiber in a direction of circumference of the outer envelope.

When an optical probe such as disclosed in Japanese Unexamined Patent Publication No. 4(1992)-135550 is inserted into an organic body, a stress change or a temperature fluctuation due to a local pressure change or a local bending of the optical fiber cannot be avoided. There has been well known the fact that when an outer pressure or a strain or a temperature change is imparted to a fiber in an interferometer which measures the interference by the use of the fibers, the refractive index of the fiber or the physical length of the fiber changes and the optical path length in the fiber changes up to 10 times the wavelength. Although, in the TD-OCT system, the difference hardly affects the resolution of the measured data since the difference is sufficiently small because the optical path length of reference light is scanned at high speed to obtain a caustic line of the interference signal. However, in the SS-OCT system or the SD-OCT system described above, strain or delete of information can be generated if the optical path length changes during measurement since the interference waveform of light is measured in the wavelength of the range with the optical path length of the reference light fixed in the SS-OCT system or the SD-OCT system.

Specifically, in the SS-OCT system, since the optical path length of one light shifts and the phase of the light shifts while the wavelength of the light source is scanned, the place shifted from the original place is observed after Fourier transform is observed, which deteriorates the resolution. Further, in the SD-OCT system, where the signals are integrally obtained, if the optical path length changes in a time shorter than the time for which the shutter is opened, there gives rise to a problem that the signals are averaged and the S/N ratio of the signal deteriorates.

SUMMARY OF THE INVENTION

In view of the foregoing observations and description, the primary object of the present invention is to provide an optical probe which can suppress deterioration in measuring accuracy due to a stress change or a temperature fluctuation because of a local pressure change or a local bending.

Another object of the present invention is to provide an optical tomography system which employs such an optical probe.

In accordance with the present invention, there is provided an optical probe comprising a tubular outer envelope, an optical fiber which is disposed in the direction of axis of the outer envelope inside the outer envelope, a light projecting means which collects light emitted from the front end of the optical fiber and projects it on a body-to-be-scanned disposed externally of the outer envelope, and a partition member which partitions the space between the outer envelope and the optical fiber and between the outer envelope and the light projecting means into an optical-path-area including the optical path of the light emanating from the light projecting means, and a non-optical-path-area, a liquid layer being formed in the non-optical-path-area.

Either liquid or gas may be filled in the optical-path-area. When liquid is filled in the optical-path-area, the liquid in the optical-path-area should have a high transmittance to the wavelength of the light and should be, for instance, water.

The partition member may be of any structure so long it partitions the space into the optical-path-area and the non-optical-path-area. For instance, the partition member may closely enclose the optical fiber and the liquid layer may be formed by filling liquid in the partition member.

An optical fiber holding portion for holding the optical member may be provided between the outer envelope and the fiber. The optical fiber may comprise only a core and a clad, or may comprise a coating member which coats the clad.

The optical probe may further comprise a pressure regulator which regulates the pressure of the liquid to be substantially constant. The optical probe may further comprise a temperature regulator which regulates the temperature of the liquid to be substantially constant.

In accordance with another aspect of the present invention, there is provided an optical tomography system characterized in that an optical probe of the present invention is employed in each of the optical tomography systems of the respective measurement systems described above. More specifically, the optical tomography system of the present invention comprises a light source which emits light, a light dividing means which divides light emitted from the light source into measuring light and reference light, a projecting optical system which projects the measuring light onto the object, a combining means which combines the reflected light from the object when the measuring light is projected onto the object and the reference light, an interference light detecting means which detects interference light of the reflected light and the reference light which have been combined by the combining means, and a tomographic image obtaining means which detects intensities of the interference light in positions in the direction of depth of the object and obtains a tomographic image of the object on the basis of the intensity of the reflected light in each position of the depth, wherein the improvement comprises that the projecting optical system includes an optical probe in accordance with the present invention.

When gas or liquid having a high transmittance to the wavelength of the light is filled in the optical-path-area, the liquid layer does not affect the light led through the optical-path-area, whereby the material of the liquid layer may have a larger heat capacity and may more suppress the stress change.

When the partition member closely confines the optical fiber and the liquid layer is formed by filling liquid in the partition member, leak of liquid from the probe outer envelope can be surely prevented.

In accordance with an optical probe and an optical tomography system employing the optical probe, since the optical probe comprises a tubular outer envelope, an optical fiber which is disposed in the direction of axis of the outer envelope inside the outer envelope, a light projecting means which collects light emitted from the front end of the optical fiber and projects it on a body-to-be-scanned disposed externally of the outer envelope, and a partition member which partitions the space between the outer envelope and the optical fiber and between the outer envelope and the light projecting means into an optical-path-area including the optical path of the light emanating from the light projecting means, and a non-optical-path-area and a liquid layer is formed in the nonoptical-path-area, when the optical probe is inserted into a living organization and a local pressure, stress change and temperature change, due to bending are applied to the optical probe, the influence on the optical fiber in the probe outer envelope can be suppressed by the pressure in the partition member, and the measuring accuracy can be prevented from deteriorating.

When an optical fiber holding portion for holding the optical member is provided between the outer envelope and the fiber, the optical fiber is prevented from adhering to the inner surface of the probe outer envelope and application of localized pressure to the optical fiber is avoided, whereby the measuring accuracy can be prevented from deteriorating.

Further, when a temperature regulator which regulates the temperature of the liquid to be substantially constant is further provided, change of the optical path length in the optical fiber can be prevented, whereby the measuring accuracy can be prevented from deteriorating.

DESCRIPTION OF THE PREFERRED EMBODIMENTS

Figure 1:
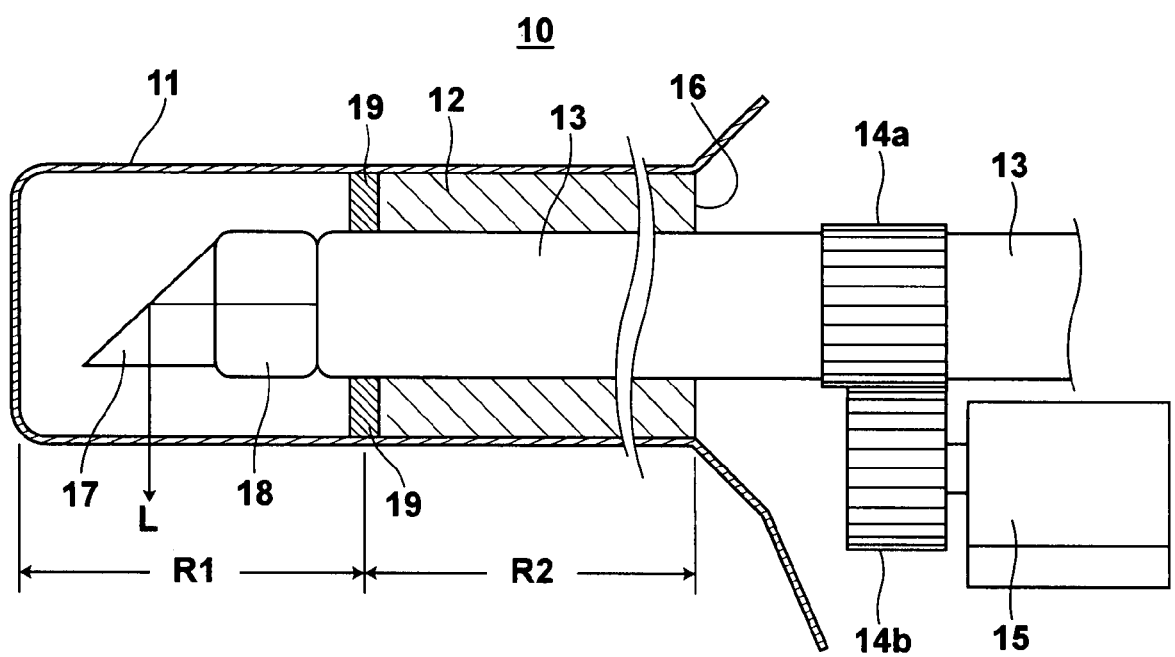
FIG. 1 is a side view partly cutaway showing an optical probe in accordance with a first embodiment of the present invention.
Figure 2:
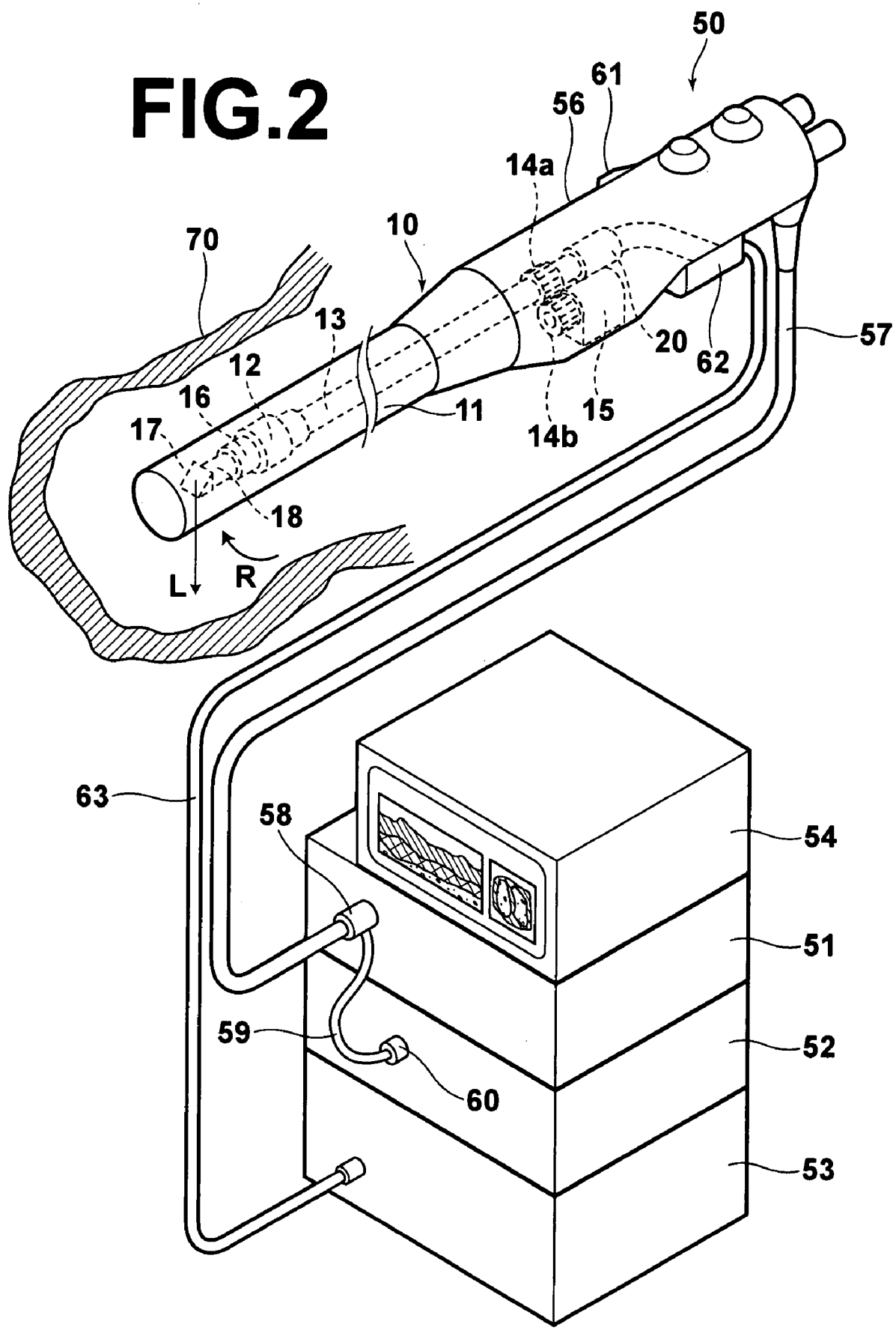
FIG. 2 is a perspective view of an optical tomographic system to which the optical probe of FIG. 1 is applied.

Embodiments of the present invention will be described in detail with reference to the drawings, hereinbelow. FIG. 1 shows a side shape partly cut-away of an optical probe 10 in accordance with a first embodiment of the present invention. The optical fiber 10, for example, forms a front end portion of an endoscope which forms a part of an optical tomography system. FIG. 2 shows an overall shape of the optical tomography system.

The optical tomography system will be first described in brief with reference to FIG. 2. The system comprises an endoscope 50 including the optical probe 10; a light source unit 51, a video processor 52, and an optical tomographic processing system 53 to which the endoscope 50 is connected; and a monitor 54 connected to the video processor 52. The endoscope 50 comprises an outer envelope 11 which is flexible and elongated, a control portion 56 connected to the rear end of the endoscope outer envelope 11 and a universal code 57 which extends outward from a side portion of the control portion 56.

A light guide (not shown) which transmits illuminating light from the light source unit 51 is passed through the universal code 57, and a light source connector 58 which is removably connected to the light source unit 51 is provided on the end of the universal code 57. A signal cable 59 extends from the light source connector 58 and a signal connector 60 which is removably connected to the video processor 52 is provided on the end of the signal cable 59. The light source unit 51 is for projecting the illuminating light onto a part of a sample 70 a tomographic image of which is to be obtained as described later.

A bight control knob 61 for controlling a bight portion provided in the probe outer envelope 11 and a light guide drive portion 62 are provided on the control portion 56, and the light guide drive portion 62 and the optical tomographic processing system 53 are connected to each other by way of a light guide 63. The probe outer envelope 11 is inserted into the sample 70 such as a human organ.

The optical probe 10 will be described with reference to FIGS. 1 and 2, hereinbelow. The optical probe 10 comprises: a cylindrical probe outer envelope 11 having a closed front end; a single optical fiber 13, which is provided inside the outer envelope 11 to extend in the direction of the axis of the outer envelope 11; and a gear 14a fixed to a part of the outer peripheral surface of the optical fiber 13, a gear 14b in mesh with the gear 14a and a motor 15 which rotates the gear 14b.

The optical probe 10 is further provided with a rod lens 18 fixed to the front end of the optical fiber 13 and a prism mirror 17 fixed to the rod lens 18. The prism mirror 17 is rotated together with the optical 13 to deflect by 900 light L emitted from the front end of the optical fiber 13 in the circumferential direction of the probe outer envelope 11, and the rod lens 18 collects light L emitted from the front end of the optical fiber 13 to converge on the sample 70 as the object to be scanned which is disposed externally of the circumference of the outer envelope 11. In this particular embodiment, the rod lens 18 and the prism mirror 17 double as a light-guide means which leads the light L reflected by the sample 70 to the front end of the optical fiber 13 to enter the optical fiber 13 from the front end as will be described later.

A partition member 19 which partitions the space formed between the probe outer envelope 11 and the optical fiber 13 and between the probe outer envelope 11 and the projecting means (the prism mirror 17 and the rod lens 18) into an optical path area R1 including the optical path of the light L emitted from the light projecting means and a non-optical path area R2. A partition member 16 is also provided in the base table of the probe outer envelope 11, and a liquid layer 12 is formed in the non-optical path area R2 closely enclosed by the partition members 16 and 19. The liquid layer 12 comprises liquid of high viscosity like an oil in order to suppress the pressure to the optical fiber 13 and smoothly rotate the same. On the other hand, a medium (e.g., air or water) which is high in transmittance to the wavelength of light L to be employed is filled in the optical path area R1.

An incident optical system 20 is disposed inside the endoscope 50 to be opposed to the base end of the optical fiber 13 as shown in FIG. 2. Light L propagating the light guide 63 and emitted from the light guide 63 is collected by the incident optical system 20 and enters the optical fiber 13 from the base end thereof.

Operation of the optical probe 10 will be described, hereinbelow. A light source such as a laser (not shown) is disposed in the optical tomographic processing system 53 shown FIG. 2, and the light L such as a laser beam emitted therefrom enters the light guide 63 and propagates therethrough. The light L entering the optical fiber 13 (FIG. 1) by way of the incident optical system 20 propagates through the optical fiber 13, is emitted from the front end thereof, is reflected by 90° by the prism mirror 17 after collected by the rod lens 18 and is emitted outside the probe 10 through the outer envelope 11 which is light-transmittable. Then when the motor 15 is driven, the optical fiber 13 rotates as described above and the prism mirror 17 and the rod lens 18 fixed thereto are rotated together with the optical fiber 13.

In response to rotation of the prism mirror 17, the light L emitted therefrom is deflected in the circumferential direction of the probe outer envelope 11, thereby scanning the sample 70 in the direction of arrow R in FIG. 2. The light L is reflected by the sample 70 while scattering and a part of the reflected light impinges upon the prism mirror 17 and is reflected toward the rod lens 18. The part of the reflected light is collected by the rod lens 18 and enters the optical fiber 13 from the front end thereof.

The reflected light thus propagating through the optical fiber 13 is emitted from the base end of the optical fiber 13, enters the light guide 63 by way of the incident optical system 20 shown in FIG. 2, and propagates through the light guide 63 to be transmitted to the optical tomographic processing system 53. In the optical tomographic processing system 53, the above described reflected light is branched from the optical path of the light L to the optical probe 10, and is detected by an optical detector (not shown). A tomographic image of the sample 70 is formed on the basis of the output of the optical detector and the tomographic image is displayed on the monitor 54.

At this time, when the liquid layer 12 is formed in the non-optical path area R2, the force applied from the probe outer envelope 11 is distributed to the whole under the Pascal's law in the liquid layer 12 even if a stress change takes place due to a local pressure change or bending generated when the optical probe 10 is inserted into a living organism or after the optical probe 10 is inserted into a living organism. Accordingly, a local stress change applied to the optical fiber 13 can be suppressed, and deterioration of, for instance, resolution by an optical path change due to a pressure change can be reduced.

Even if a temperature change, especially a temperature change which is localized and sharp, takes place in response to insertion of the optical probe 10 into a living organism, the localized temperature change is dispersed by the heat capacity of the overall liquid layer 12 and the response time can be delayed. By this, the influence on the data strain of the OCT system can be reduced.

Second to fifth embodiments of the present invention will be described with reference to FIGS. 3 to 6, hereinbelow. In FIGS. 3 to 6, the elements analogous to those in FIGS. 1 and 2 are given the same reference numerals and will not be described unless necessary.

The second embodiment of the present invention will be first described with reference to FIG. 3. In the optical probe 100 of the second embodiment, a partition member 112 is provided to closely enclose the optical fiber 13, and the liquid layer 12 is formed by filling liquid in the partition member 112. That is, a non-optical-path area R2 formed by filling a liquid is formed between the partition member 112 and the optical fiber 13 and a vacant space is formed between the partition member 112 and the optical fiber 13. The partition member 112 is rotated together with the optical fiber 13. With this arrangement, the liquid can be prevented from escaping outside in case that the probe outer envelope 11 is damaged.

Figure 3:
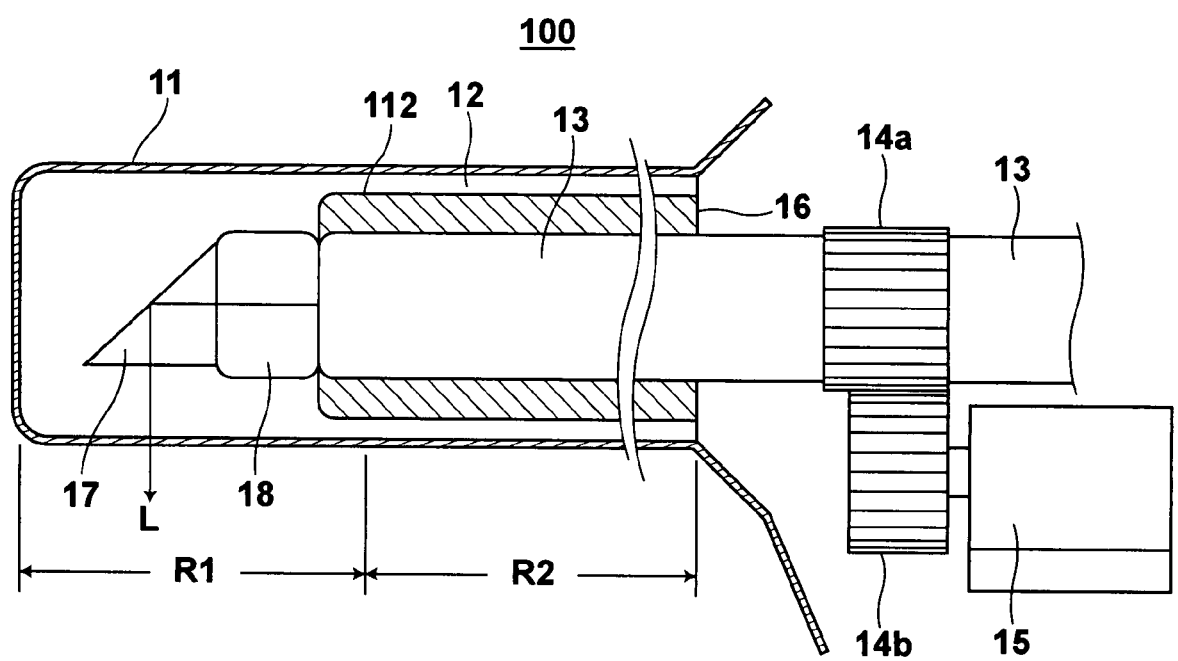
FIG. 3 is a side view partly cutaway showing an optical probe in accordance with a second embodiment of the present invention.

Although, in FIG. 3, the partition member 112 is provided on the optical fiber 13 over substantially the entire range of the longitudinal direction thereof, the partition member 112 closely enclosing liquid may be provided in only the part where it has been empirically known that the bending stress is apt to be generated.

A third embodiment of the present invention will be described with reference to FIGS. 4A to 4C, hereinbelow. In the optical probe 120 of the third embodiment, a fiber holding member 121 is provided between the probe outer envelope 11 and the optical fiber 13. The fiber holding member 121 extends from the inner surface of the probe outer envelope 11 toward the center and fixes the optical fiber 13 to the vicinity of the center of the probe outer envelope 11. By thus providing the fiber holding member 121, the optical fiber 13 is prevented from adhering to the inner surface of the probe outer envelope 11 and application of localized pressure to the optical fiber 13 is avoided, whereby the measuring accuracy can be prevented from deteriorating. The fiber holding member 121 may be of soft material so that it also functions as a cushion member.

Figure 4A:
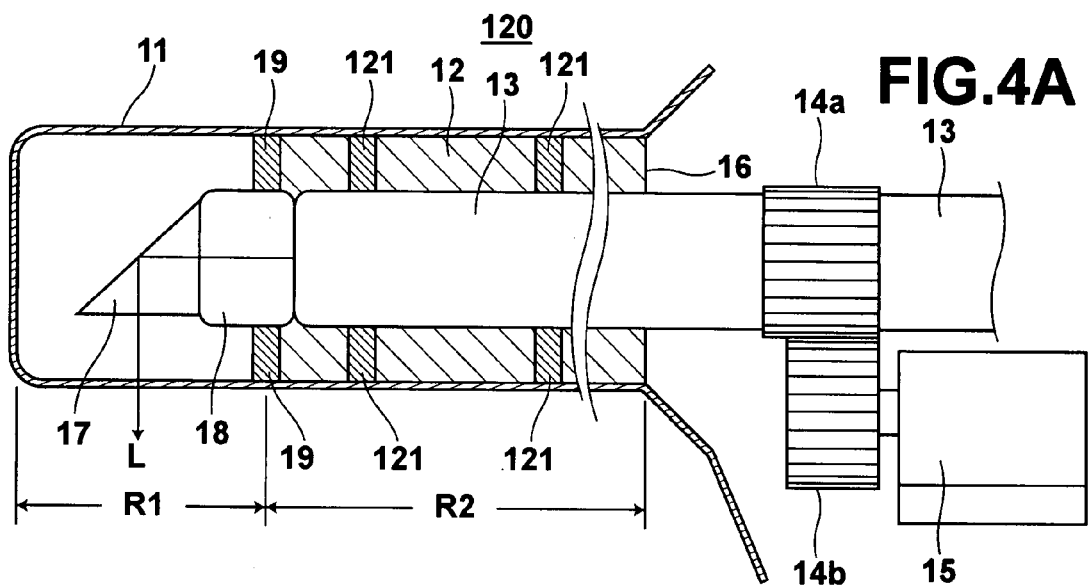
FIGS. 4A to 4C are side views partly cutaway showing an optical probes in accordance with a third embodiment of the present invention and modification thereof.
Figure 4B:
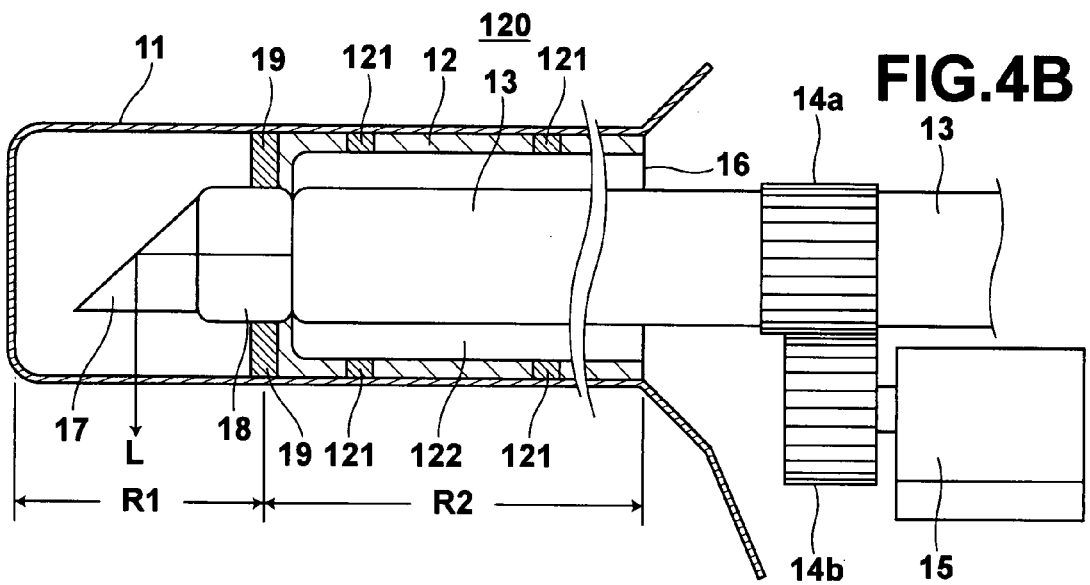
Figure 4C:
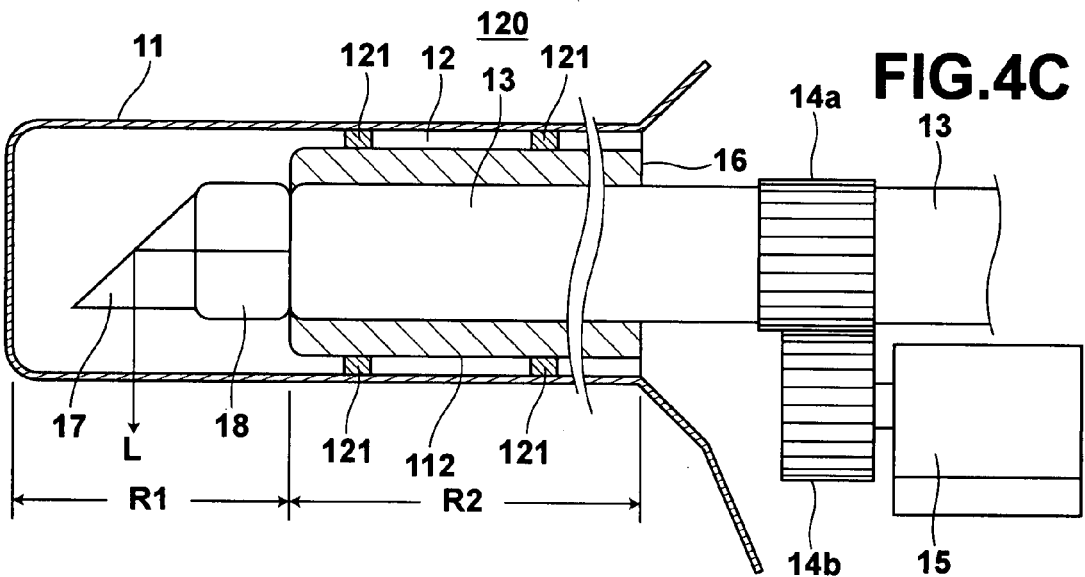

Although, in FIG. 4A, the fiber holding member 121 is in a direct contact with the optical fiber 13, the optical fiber 13 may be coated with a coating member 122 and the fiber holding member 121 may hold the coating member 122 as shown in FIG. 4B. Further, instead of the above-described coating member 122, the partition member 112 closely enclosing a liquid may be employed as shown in FIG. 4C. With this arrangement, one of the liquid or the coating member 122 functions as a cushion member and the optical fiber can be prevented from being damaged even if a localized pressure is generated.

Figure 5:
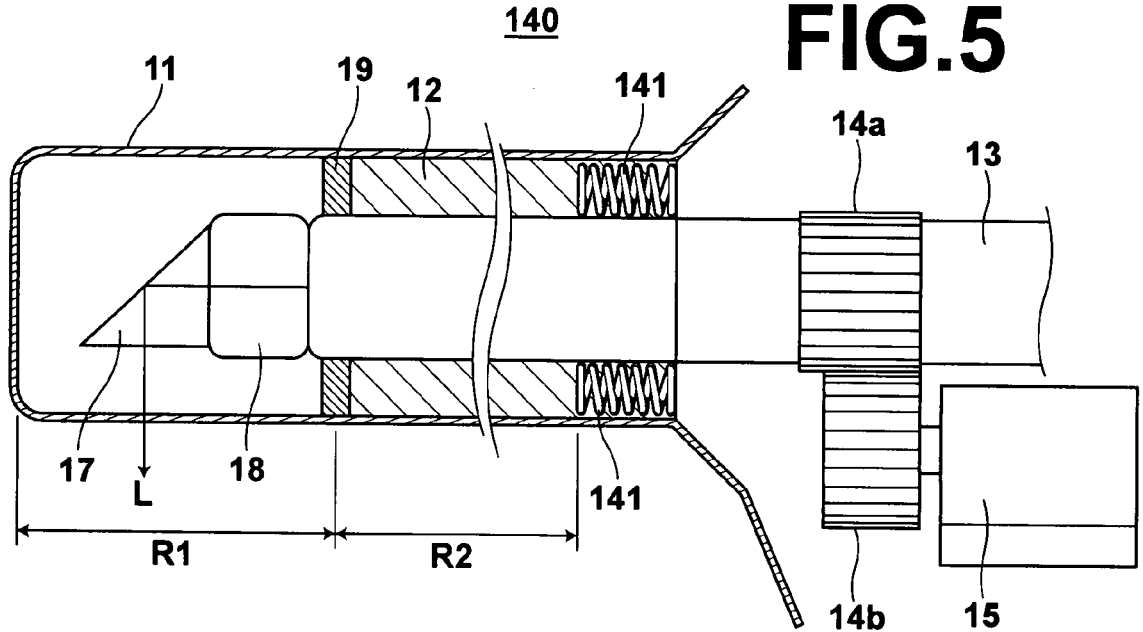
FIG. 5 is a side view partly cutaway showing an optical probe in accordance with a fourth embodiment of the present invention.

A fourth embodiment of the present invention will be described with reference to FIG. 5, hereinbelow. In the optical probe 140 of the fourth embodiment, a pressure regulator 141 which holds constant the pressure of the liquid layer 12 in the probe outer envelope 11 is provided. The pressure regulator 141 comprises, for instance, a spring connected to the partition member 16, and holds constant the internal pressure of the liquid layer 12 by compressing the spring when a pressure is applied from the external of the probe outer envelope 11, thereby dispersing constant the pressure applied to the optical fiber 13. With this arrangement, the stress change due to the localized pressure described above or the bending of the optical fiber can be absorbed by the pressure regulator 141, and the measuring accuracy can be prevented from deteriorating.

Although, in the illustrated embodiment, the pressure regulator 141 comprises a spring, the pressure regulator 141 may be of any mechanism such as a hydraulic mechanism or a pneumatic mechanism so long as it is employed to generally adjust a pressure. Further, by forming the partition member from rubber-like material having an elasticity, the partition member itself may be caused to function as a pressure regulator 141.

Figure 6:
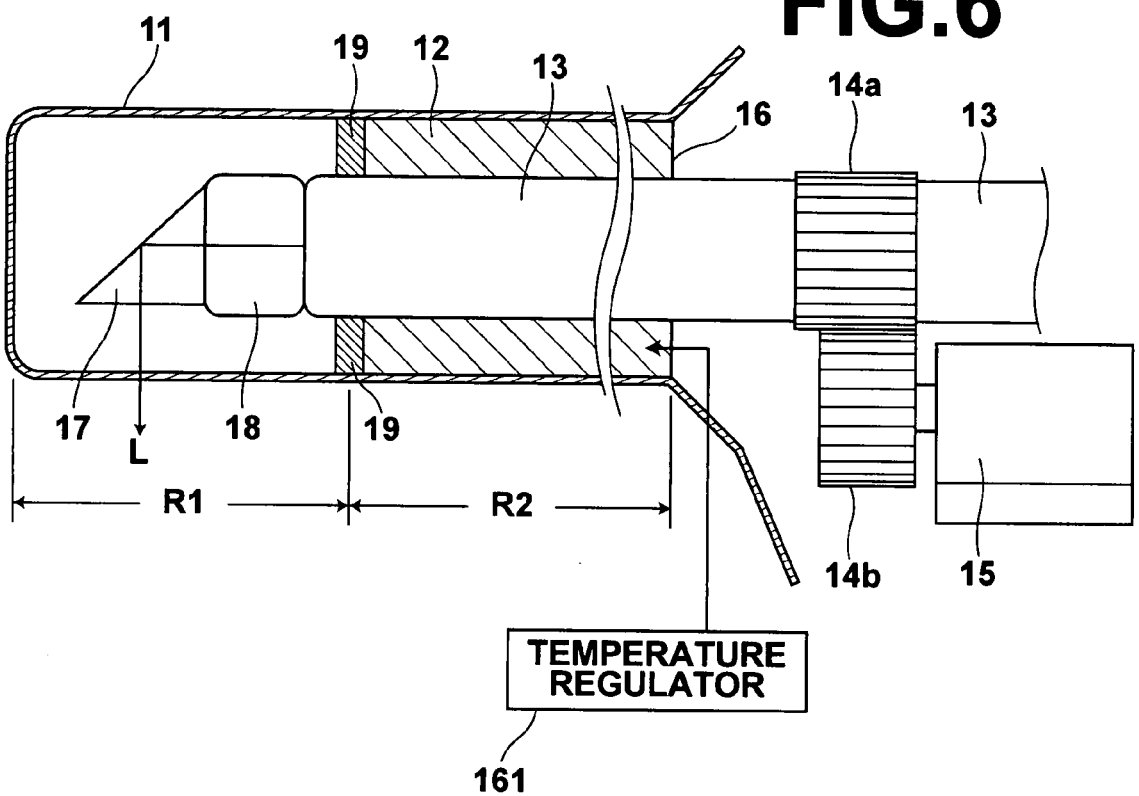
FIG. 6 is a side view partly cutaway showing an optical probe in accordance with a fifth embodiment of the present invention.

A fifth embodiment of the present invention will be described with reference to FIG. 6, hereinbelow. In the optical probe 160 of the fifth embodiment, a temperature regulator 161 which regulates the temperature of the liquid in the liquid layer 12 to be substantially constant is provided. The temperature regulator 161 regulates the temperature of the liquid in the liquid layer 12 to be substantially constant by heating/cooling the liquid layer or by circulating the liquid in the liquid layer 12 between an external reservoir (not shown). With this arrangement, temperature fluctuation of the optical fiber 13 is suppressed and the optical path length change is prevented, whereby deterioration of measurement accuracy can be prevented. Although, in the embodiment illustrated in FIG. 6, the probe outer envelope 11 is filled with liquid, the temperature of the liquid filled in the partition member 112 may be similarly regulated to be substantially constant.

Figure 7:
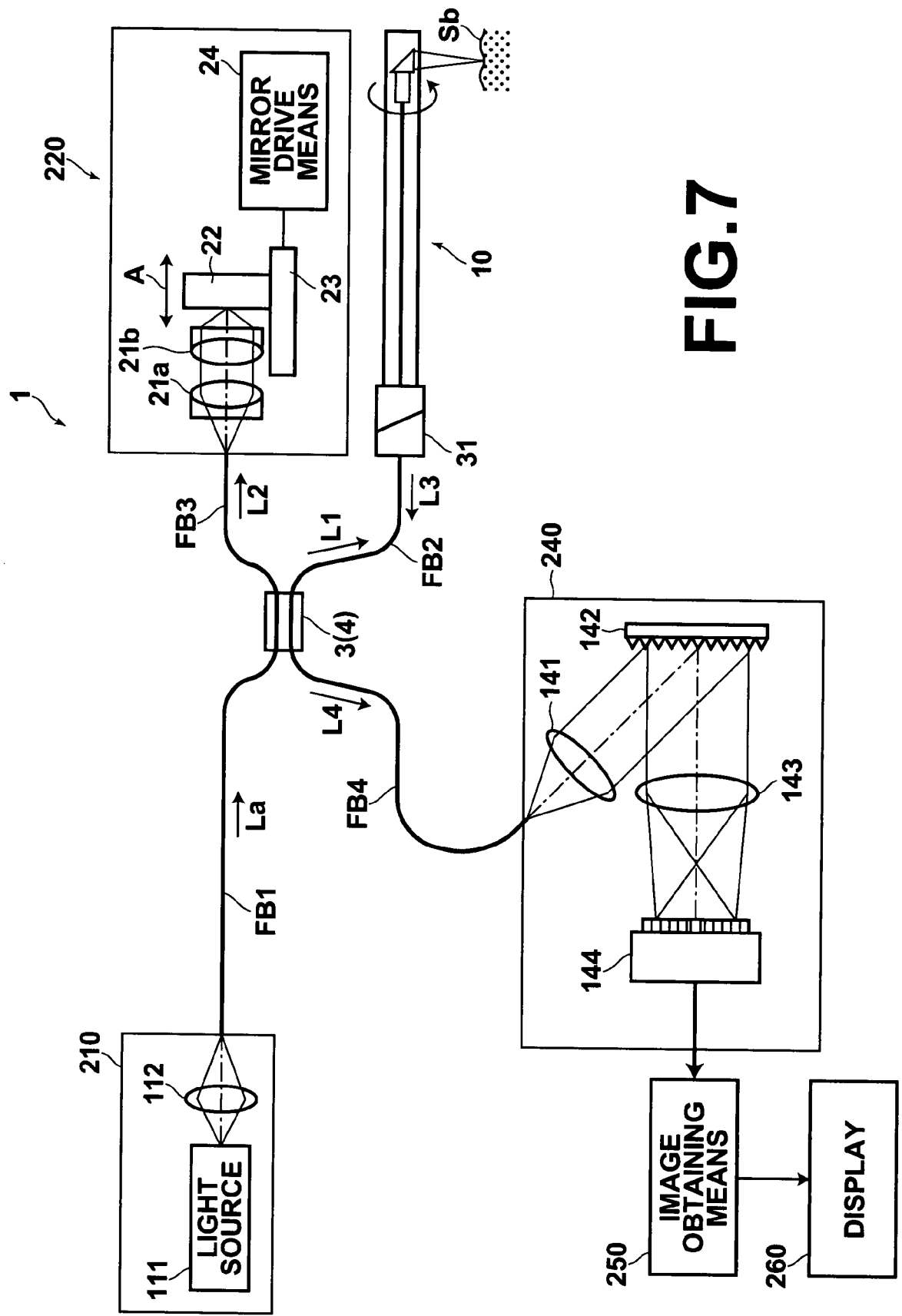
FIG. 7 is a schematic view showing an example of the optical tomography system by the SD-OCT measurement to which the optical probe of the present invention is applied.

Examples of the optical tomography system to which the optical probes of the present invention are to be applied will be described, hereinbelow. The optical tomography system 1 shown in FIG. 7 is for obtaining a tomographic image of an object of measurement such as a living tissue or a cell in a body cavity by measuring the SD-OCT. The optical tomography system 1 comprises: a light source unit 210 which emits light La; a light dividing means 3 which divides the light La emitted from the light source unit 210 into measuring light L1 and reference light L2; an optical path length adjusting means 220 which adjusts the optical path length of the reference light L2 divided by the light dividing means 3; an optical probe 10 which guides to the object Sb to be measured the measuring light beam L1 divided by the light dividing means 3; a combining means 4 for combining a reflected light beam L3 from the object Sb when the measuring light beam L1 is irradiated onto the object Sb from the probe 10, and the reference light beam L2; and an interference light detecting means 240 for detecting interference light beam L4 of the reflected light beam L3 and the reference light beam L2 which have been combined by the combining means 4.

The light source unit 210 comprises a light source 111 which emits low coherence light La such as an SLD (super luminescent diode), ASE (amplified spontaneous emission) or a super continuum where an ultra short pulse laser beam is projected onto a nonlinear medium to obtain broad band light and an optical system 112 which enters the light emitted from the light source 111 into an optical fiber FB1.

The light dividing means 3 comprises, for instance, a 2×2 fiber optic coupler and divides the light beam La led thereto by way of the optical fiber FB1 from the light source unit 210 into the measuring light beam L1 and the reference light beam L2. The light dividing means 3 is optically connected to two optical fibers FB2 and FB3, and the measuring light beam L1 is propagated through the optical fiber FB2 while the reference light beam L2 is propagated through the optical fiber FB3. In this embodiment, the light dividing means 3 also functions as the combining means 4.

The optical probe 10 previously shown in FIG. 1 is optically connected to the optical fiber FB2 and the measuring light beam L1 is guided to the probe 10 from the optical fiber FB2. The probe 10 is inserted into a body cavity, for instance, through a forceps port by way of a forceps channel and is removably mounted on the optical fiber FB2 by an optical connector 31.

The optical path length adjusting means 220 is disposed on the side of the optical fiber FB3 radiating the reference light beam L2. The optical path length adjusting means 220 changes the optical path length of the reference light beam L2 in order to adjust an initiating position of a range over which a tomographic image is to be obtained and comprises a reflecting mirror 22 which reflects the reference light beam L2 radiated from the optical fiber FB3, a first lens 21a disposed between the reflecting mirror 22 and the optical fiber FB3, and a second lens 21b disposed between the first lens 21a and the reflecting mirror 22.

The first lens 21a makes parallel the reference light beam L2 radiated from the core of the optical fiber FB3 and at the same time, collects the reference light beam L2 reflected by the reflecting mirror 2 on the core of the optical fiber FB3. The second lens 21b collects the reference light beam L2 made parallel by the first lens 21a on the reflecting mirror 22 and at the same time, makes parallel the reference light beam L2 reflected by the reflecting mirror 22. That is, the first and second lenses 21a and 21b form a confocal optical system.

Accordingly, the reference light beam L2 radiated from the optical fiber FB3 is turned to a parallel light by the first lens 21a and is collected on the reflecting mirror 22 by the second lens 21b. Subsequently, the reference light beam L2 reflected by the reflecting mirror 22 is turned to a parallel light by the second lens 21b and is collected on the core of the optical fiber FB3 by the first lens 21a.

The optical path length adjusting means 220 is further provided with a base table 23 to which the second lens 21b and the reflecting mirror 22 are fixed and a mirror movement means 24 which moves the base table 23 in the direction of the optical axis of the first lens 21a. In response to movement of the base table 23 in the direction of arrow A, the optical path length of the reference light beam L2 can be changed.

The combining means 4 comprises a 2×2 fiber optic coupler as described above, and combines the reference light beam L2 which has been shifted in its frequency and has been changed in its optical path length by the optical path length adjusting means 220 and the reflected light beam L3 from the object Sb to emit the combined light beam toward the interference light detecting means 240 by way of an optical fiber FB4.

The interference light detecting means 240 detects interference light L4 of the reflected light beam L3 and the reference light beam L2 which have been combined by the combining means 4, and comprises a collimator lens 141 which makes parallel the interference light beam L4 radiated from the optical fiber FB4, a spectral means 142 which divides the interference light beam L4, having a plurality of wavelength bands, by the wavelength bands and a light detecting means 144 which detects each wavelength band of the interference light beam L4 divided by the spectral means 142.

The spectral means 142 comprises, for instance, a diffraction grating element, and spectrally divides the interference light beam L4 entering it to output the divided interference light beam L4 to the light detecting means 144. The light detecting means 144 is formed by, for instance, a CCD element which comprises a plurality of, for instance, one-dimensionally or two-dimensionally arranged photosensors and each of the photosensors detects each wavelength band of the interference light beam L4 spectrally divided as described above.

The light detecting means 144 is connected to an image obtaining means 250 comprising, for instance, a computer system such as a personal computer. The image obtaining means 250 is connected to a display system 260 formed, for instance, by a CRT or a liquid crystal display system.

Operation of the optical tomography system 1 having a structure described above will be described, hereinbelow. When a tomographic image is to be obtained, the optical path length is first adjusted by moving the base 23 in the direction of the arrow A so that the object Sb is positioned in the measurable area. The light beam La is emitted from the light source unit 210 and the light beam La is divided into the measuring light beam L1 and the reference light beam L2 by the light dividing means 3. The measuring light beam L1 is radiated from the optical probe 10 toward a body cavity and is projected onto the object Sb. At this time, the measuring light beam L1 radiated from the optical probe 10 is caused to one-dimensionally scan the object Sb by the optical probe 10 operating as described above. Then the reflected light beam L3 from the object Sb and the reference light beam L2 reflected by the reflecting mirror 22 are combined, and the interference light beam L4 of the reflected light beam L3 and the reference light beam L2 is detected by the interference light detecting means 240. Information on the intensity distribution of the reflected light in the direction of depth of the object Sb is obtained by carrying out Fourier transform on the detected interference light beam L4 in the image obtaining means 250 after carrying out a suitable waveform compensation and noise removal.

By causing the measuring light beam L1 to scan the object Sb by the optical probe 10 as described above, information on the direction of depth of the object Sb along the direction of scan is obtained and accordingly tomographic images on the cross-section including the direction of scan can be obtained. The tomographic images thus obtained are displayed by the display system 260. Further, for instance, by moving the optical probe 10 right and left in FIG. 7 so that the measuring light L1 scans the object Sb in a second direction perpendicular to said direction of scan, tomographic images on the cross-section including the second direction can be further obtained.

Figure 8:
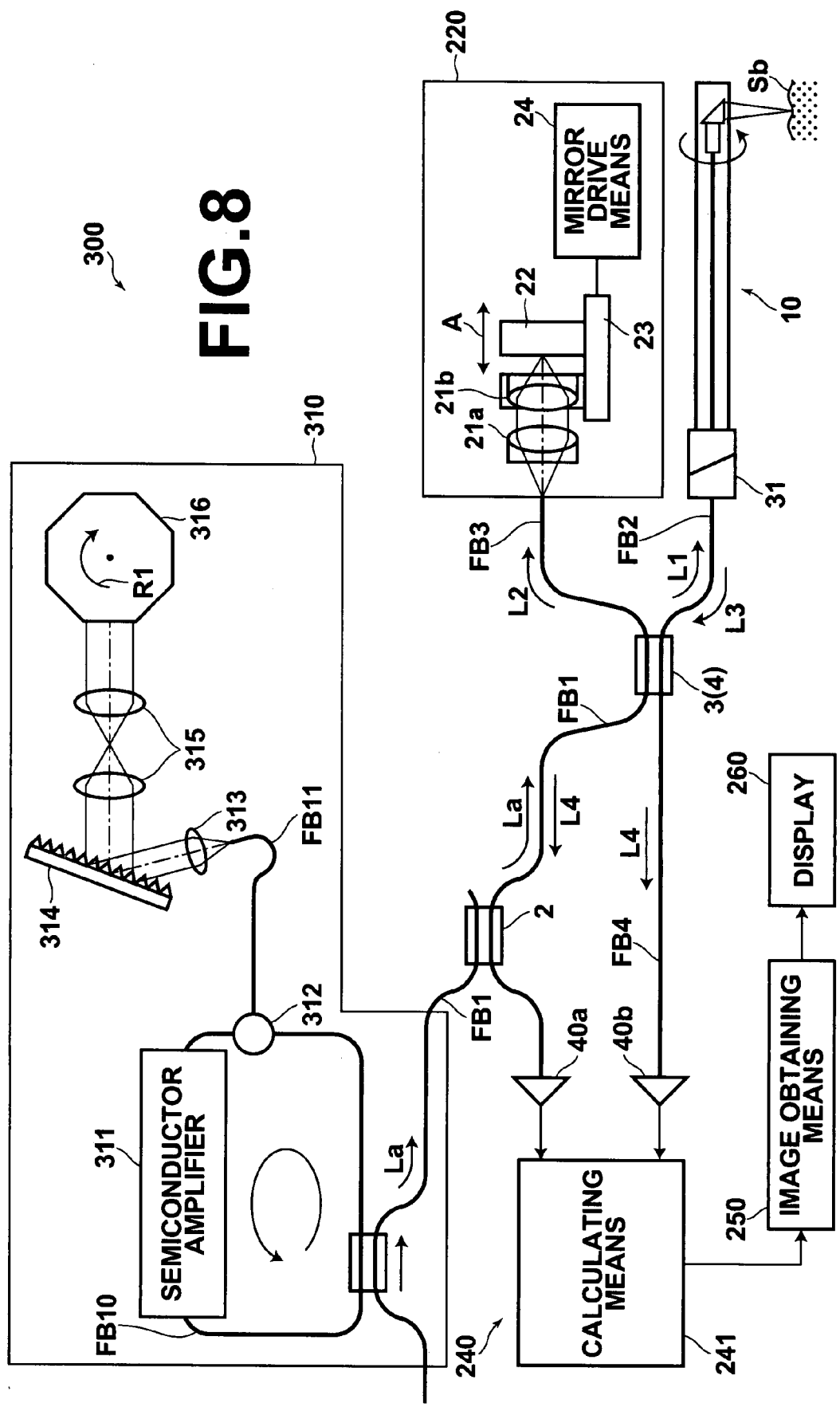
FIG. 8 is a schematic view showing an example of the optical tomography system by the SS-OCT measurement to which the optical probe of the present invention is applied.

Another example of the optical tomography system to which the optical probes of the present invention are to be applied will be described, hereinbelow. The optical tomography system 300 shown in FIG. 8 is for obtaining a tomographic image of the object of measurement by measuring the SS-OCT and specifically differs from the optical tomography system 1 shown in FIG. 7 in structure of the light source unit and the interference light detecting means.

The light source unit 310 of this system emits a laser beam La while sweeping its wavelength at a predetermined period. Specifically, the light source unit 310 comprises a semiconductor optical amplifier (a semiconductor gain medium) 311 and an optical fiber FB10 connected to the semiconductor optical amplifier 311 at opposite ends thereof. The semiconductor optical amplifier 311 emits weak light to one end of the optical fiber FB10 in response to injection of a drive current and amplifies light input from the other end of the optical fiber FB10. When a drive current is supplied to the semiconductor optical amplifier 311, a pulse-like laser beam La is emitted to the optical fiber FB1 by a resonator formed by the semiconductor optical amplifier 311 and the optical fiber FB10.

Further, an optical divider 312 is connected to the optical fiber FB10 and a part of the light beam propagated through the optical fiber FB10 is emitted from the optical divider 312 toward the optical fiber FB11. Light emitted from the optical fiber FB11 travels through the collimator lens 313, the diffraction grating element 314 and the optical system 315 and is reflected by the rotating polygon mirror 316. The reflected light is returned to the optical fiber FB11 by way of the optical system 315, the diffraction grating element 314 and the collimator lens 313.

The rotating polygon mirror 316 rotates in the direction indicated by arrow R1, to vary the angle of each reflective surface thereof with respect to the optical axis of the optical system 315. Thereby, only a light beam having a specific frequency, among the light spectrally split by the diffraction grating 314, is returned to the optical fiber FB11. The frequency of the light beam that reenters the optical fiber FB1 is determined by the angle formed by the optical axis of the optical system 315 and the reflective surface of the rotating polygon mirror 316. Then the light beam of a specific frequency band impinging upon the optical fiber FB11 enters the optical fiber FB10, and as a result, only a laser beam La of the specific frequency band is emitted toward the optical fiber FB1.

Accordingly, when the rotating polygon mirror 316 rotates in the direction indicated by arrow R1 at a constant speed, the wavelength $\lambda$ of the light beam which reenters the optical fiber FB11 changes at a period with time. As a result, a laser beam La which is swept in its wavelength is emitted from the light source unit 310 toward the optical fiber FB1.

The interference light detecting means 240 detects interference light beam L4 of the reflected light beam L3 and the reference light beam L2 which have been combined by the combining means 4 and the image obtaining means 250 detects the intensities of the reflected light beam L3 in positions in the direction of depth of the object Sb by carrying out Fourier transform on the interference light beam L4 detected by the interference light detecting means 240 and obtains a tomographic image of the object Sb. The tomographic images thus obtained are displayed by the display system 260. In this embodiment, a mechanism where the interference light L4 is divided into a pair of lights by the fiber coupler which are guided to optical detectors 40a and 40b and a balanced detection is carried out in a calculating means 241 is formed. As can be understood, in this embodiment, the interference light detecting means 240 is formed by the optical detectors 40a and 40b and the calculating means 241.

Here, detection of the interference light beam L4 in the interference light detecting means 240 and image generation in the image obtaining means 250 will be described briefly. Note that a detailed description of these two points can be found in "Optical Frequency Scanning Interference Microscopes", M. Takeda, *Optics Engineering Contact*, Vol. 41, No. 7, pp. 426-432, 2003.

When the measuring light beam L1 is projected onto the object Sb, the reflected light L3 from each depth of the object Sb and the reference light L2 interfere with each other with various optical path length difference l. When the light intensity of the interference fringe at this time versus each optical path length difference is assumed to be S(l), the light intensity I(k) detected in the interference light detecting means 240 is expressed by the following formula.

$$I(k)=\int_0^\infty S(l)[l+\cos(kl)]dl$$

wherein k represents the wave number and l represents the optical path length difference. The above formula may be considered to be given as an interferogram of a light frequency range having a wave number of $\omega/c$ ($k=\omega/c$) as a variable. Accordingly, a tomographic image is generated by obtaining in the image obtaining means 250 information on the distance of the object Sb from the measurement initiating position and information on the intensity of reflection by carrying out Fourier-transform on the spectral interference fringes detected by the interference light detecting means 240 and determining the intensity S(l) of the interference light beam L4.

In the optical tomography system 300, an optical probe 10 the same in arrangement as that employed in the system of FIG. 7 is employed and the operation is the same as that employed in the system of FIG. 7.

Figure 9:
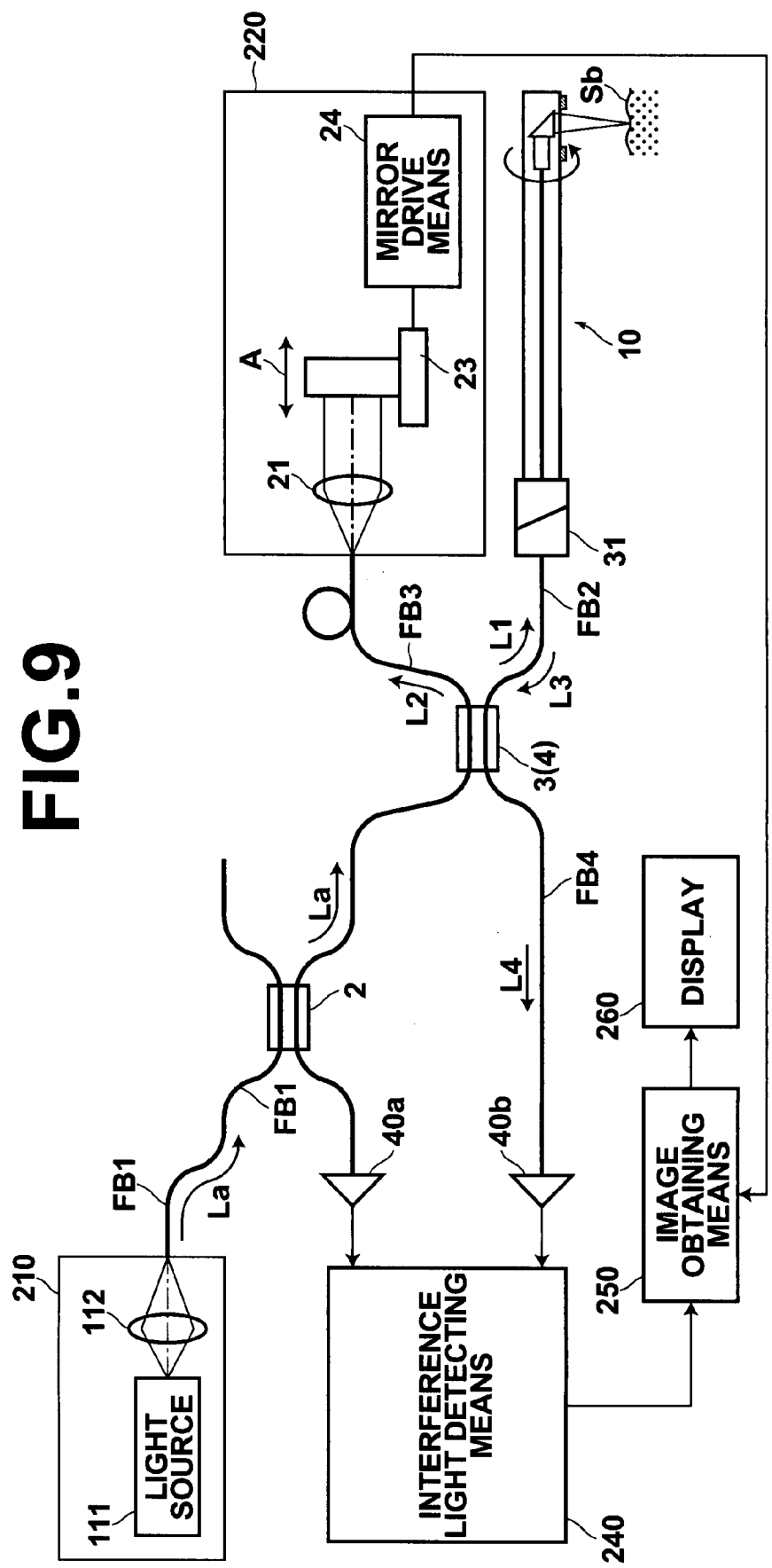
FIG. 9 is a schematic view showing an example of the optical tomography system by the TD-OCT measurement to which the optical probe of the present invention is applied.

Still another example of the optical tomography system to which the optical probes of the present invention are to be applied will be described, hereinbelow. The optical tomography system 400 shown in FIG. 9 is for obtaining a tomographic image of the object of measurement by measuring the TD-OCT and comprises a light source unit 210 provided with a light source 111 which emits laser light La and a light collecting lens 112, a light dividing means 2 which divides a laser light La emitted from the light source unit 210 and propagated through the optical fiber FB1, a light dividing means 3 which divides the laser light La passing therethrough into measuring light L1 and reference light L2, an optical path length adjusting means 220 which adjusts the optical path length of the reference light L2 divided by the light dividing means 3 and propagated through the optical fiber FB3, an optical probe 10 which projects onto the object Sb the measuring light L1 divided by the light dividing means 3 and propagated through the optical fiber FB2, a combining means 4 (the light dividing means 3 doubles) which combines the reflected light L3 from the object Sb when the measuring light L1 divided by the light dividing means is projected onto the object Sb and the reference light L2, and an interference light detecting means 240 which detects interference light L4 of the reflected light L3 and the reference light L2 which have been combined by the combining means 4.

The optical path length adjusting means 220 comprises a collimator lens 21 which makes parallel the reference light beam L2 radiated from the optical fiber FB3, a reflecting mirror 23 which is movable in the direction of arrow A to change the distance from the collimator lens 21, and a mirror moving means 24 which moves the reflecting mirror 23 and changes the optical path length of the reference light L2 in order to change the measuring position in the object Sb in the direction of depth. The reference light L2 which has been changed in its optical path length by the optical path length adjusting means 220 is guided to the combining means 4.

The interference light detecting means 240 detects the intensity of the interference light L4 propagating through the optical fiber FB2 from the combining means 4. Specifically, only when the optical length difference between the sum of the total optical path length of the measuring light L1 and the optical path length of the reflected light L3 reflected or scattered rearward at a certain point on the object Sb and the reference light L2 is smaller than the coherence length of the light source, an interference signal whose amplitude is proportional to the amount of the reflected light is detected. Further, as the optical path length is scanned by the optical path length adjusting means 220, the position of the reflecting point (depth) in which the interference signal is obtained is changed, whereby the interference light detecting means 240 detects a reflectance signal in each measuring position of object Sb. Information on the measuring position is output from the optical path length adjusting means 220 to the image obtaining means. On the basis of the signals detected by the interference light detecting means 240 and information on the measuring position in the mirror moving means 24, information on the intensity distribution of the reflected light in the direction of depth of the object Sb is obtained by the image obtaining means 250.

By causing the measuring light beam L1 to scan the object Sb by the optical probe 10 as described above, information on the direction of depth of the object Sb is obtained and accordingly tomographic images on the cross-section including the direction of scan can be obtained. The tomographic images thus obtained are displayed by the display system 260. Further, for instance, by moving the optical probe 10 right and left in FIG. 7 so that the measuring light L1 scans the object Sb in a second direction perpendicular to said direction of scan, tomographic images on the cross-section including the second direction can be obtained.

In the optical tomography system 400, an optical probe 10 the same in arrangement as that employed in the system of FIG. 7 is also employed and the operation is the same as that employed in the system of FIG. 7.

Although the optical tomography systems 1, 300 and 400 in which the optical probe 10 is employed, the optical probes 100, 120, 140 and 160 in accordance with previously described other embodiments of the present invention may be, of course, employed instead of the optical probe 10.

What is claimed is:

1. An optical probe comprising
a tubular outer envelope,
an optical fiber which is disposed in the direction of axis of the outer envelope inside the outer envelope,
a light projecting means which collects light emitted from the front end of the optical fiber and projects it on a body-to-be-scanned disposed externally of the outer envelope, a partition member which partitions the space within the tubular outer envelope into an optical path area and a non-optical path area,
wherein the optical path area includes the optical path of the light projected from the light projecting means and is comprised of the space between the tubular outer envelope and the light projecting means,
wherein the non-optical path area is comprised of the space between the tubular outer envelope and at least a portion of the optical fiber;
wherein a liquid layer is formed in the non-optical path area, and
wherein a liquid having a high transmittance to the wavelength of the light is filled in the optical-path-area.

2. An optical probe as defined in claim 1, wherein the liquid comprising the liquid layer formed in the non-optical path area is different from the liquid filled in the optical path area.

3. An optical probe as defined in claim 1, wherein a liquid comprising the liquid layer formed in the non-optical path area has a higher viscosity than the liquid filled in the optical path area.

* * * * *